United States Patent
Lührs et al.

(10) Patent No.: US 6,749,640 B1
(45) Date of Patent: Jun. 15, 2004

(54) MULTIAXIS JOINT, ESPECIALLY ARTIFICIAL KNEE JOINT

(75) Inventors: Bernd Lührs, Bueren (DE); Frank Theile, Dimelsee Adorf (DE); Michael Griesser, Salzkotten (DE); Hans Albert Richard, Paderborn (DE); Gunter Kullmer, Altenbeken-Schwaney (DE)

(73) Assignee: Heggemann GmbH, Bueren (DE)

( * ) Notice: Subject to any disclaimer, the term of this patent is extended or adjusted under 35 U.S.C. 154(b) by 0 days.

(21) Appl. No.: 10/168,361
(22) PCT Filed: Nov. 24, 2000
(86) PCT No.: PCT/DE00/04180
§ 371 (c)(1), (2), (4) Date: Jul. 23, 2002
(87) PCT Pub. No.: WO01/45596
PCT Pub. Date: Jun. 28, 2001

(30) Foreign Application Priority Data

Dec. 21, 1999 (DE) .......................... 199 61 915
May 29, 2000 (DE) .......................... 100 26 440

(51) Int. Cl.[7] ................................ A61F 2/64
(52) U.S. Cl. ........................... 623/39; 623/44
(58) Field of Search ................. 623/39, 41, 42, 623/43, 44, 45

(56) References Cited

U.S. PATENT DOCUMENTS

| | | | |
|---|---|---|---|
| 3,823,424 A | | 7/1974 | May ........................ 3/22 |
| RE33,621 E | * | 6/1991 | Lamb et al. .............. 128/80 |
| 5,314,498 A | | 5/1994 | Gramnäs .................. 623/39 |
| 5,728,173 A | | 3/1998 | Chen ....................... 623/44 |
| 5,888,236 A | * | 3/1999 | van de Veen ............. 623/44 |
| 5,904,721 A | | 5/1999 | Henry et al. .............. 623/26 |
| 6,206,933 B1 | * | 3/2001 | Shorter et al. ............ 623/44 |

FOREIGN PATENT DOCUMENTS

| | | |
|---|---|---|
| DE | 841 190 | 4/1952 |
| EP | 0 590 386 | 4/1994 |
| EP | 0 947 182 | 10/1999 |
| FR | 1 187 444 | 9/1959 |
| GB | 1 533 796 | 11/1978 |

* cited by examiner

Primary Examiner—Bruce Snow
(74) Attorney, Agent, or Firm—Cohen, Pontani, Lieberman & Pavane

(57) ABSTRACT

A lower platform and an upper platform are connected first and second levers having different lengths, each lever being articulated about a first axis on said lower platform and a second axis on said upper platform. The upper platform can be swiveled from a rest position to a position of maximum excursion relative to the lower platform so that the distance between platforms is immediately reduced upon swiveling from the rest position. At least one axis is provided with a brake which slows down rotational movement.

28 Claims, 8 Drawing Sheets

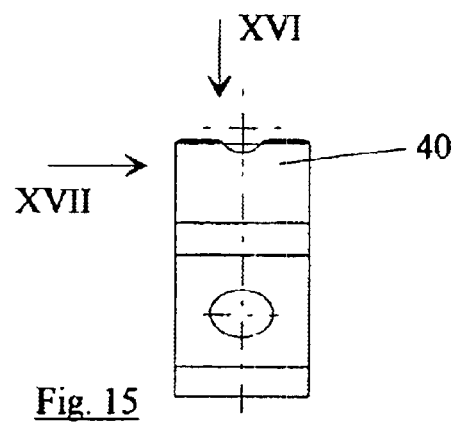
Fig. 15
Fig. 16
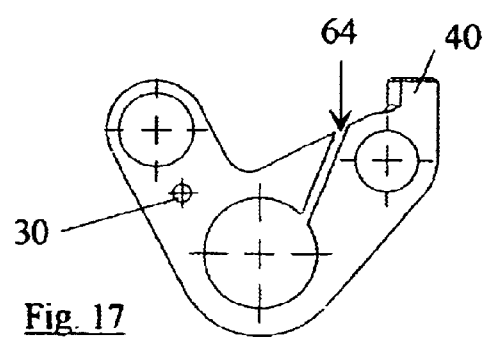
Fig. 17
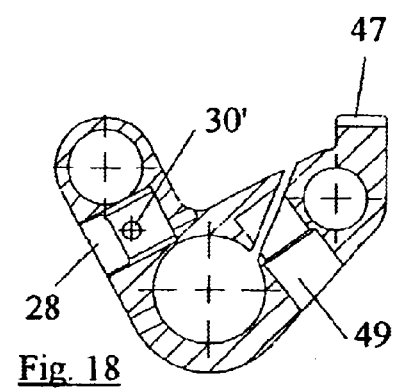
Fig. 18
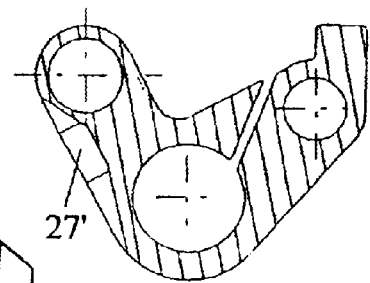
Fig. 19
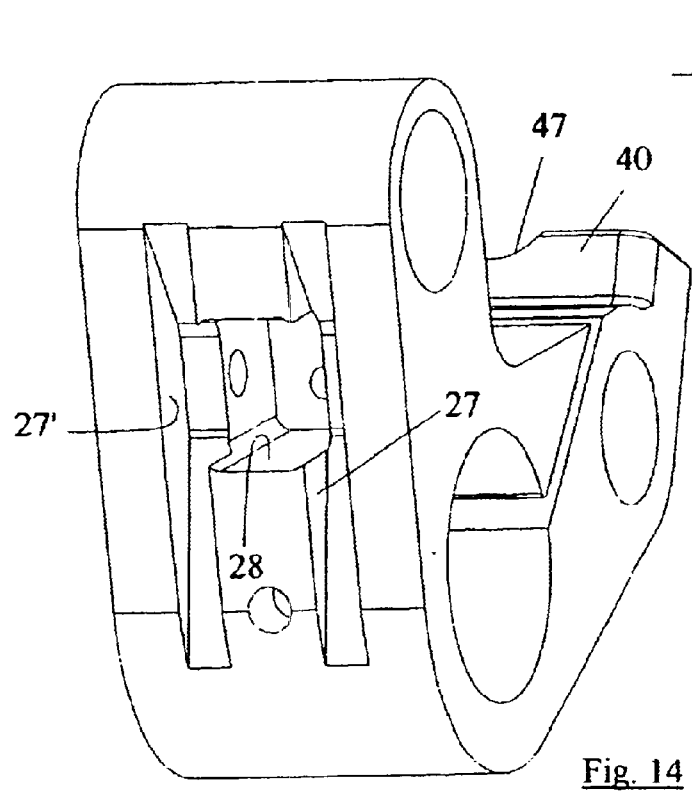
Fig. 14

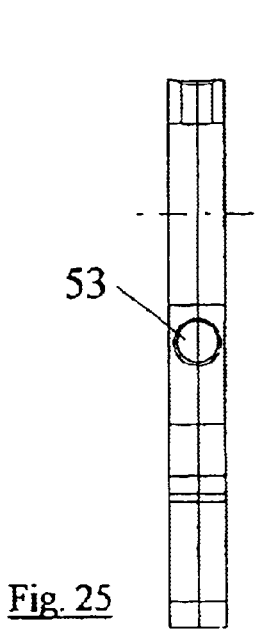
Fig. 25
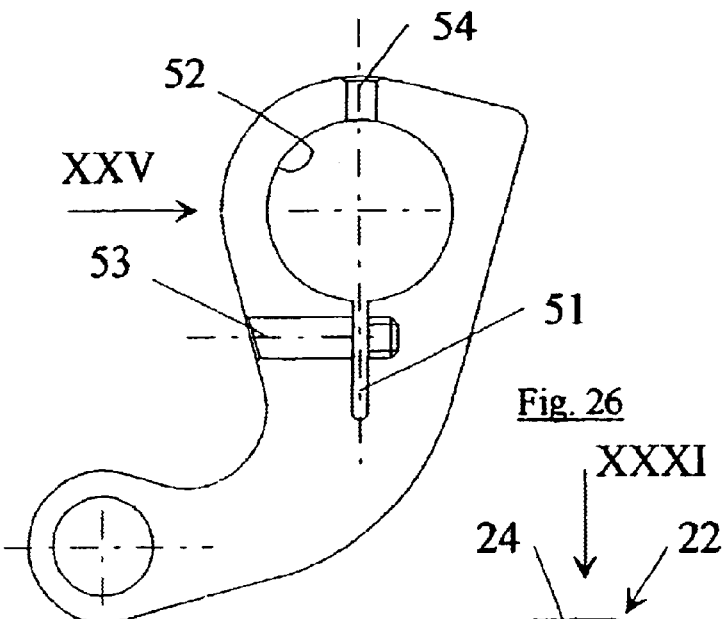
Fig. 26
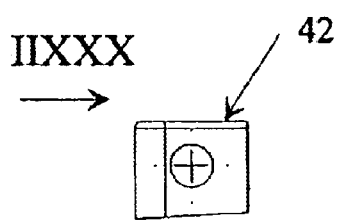
Fig. 27
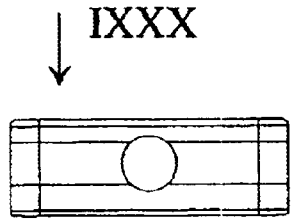
Fig. 28
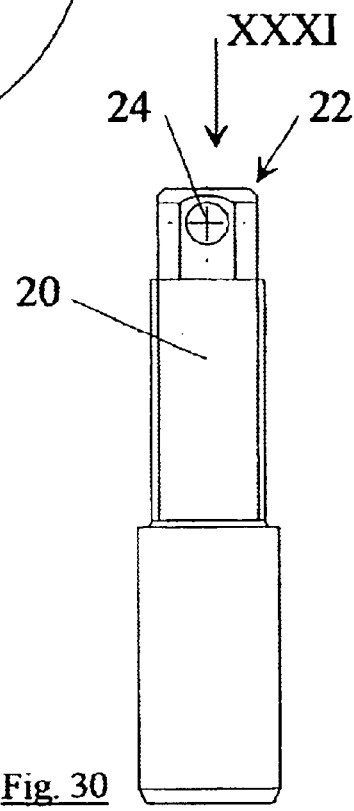
Fig. 30
Fig. 29
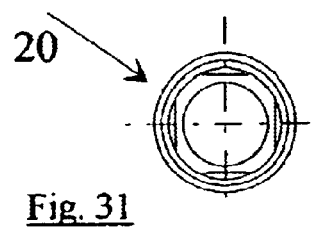
Fig. 31

MULTIAXIS JOINT, ESPECIALLY ARTIFICIAL KNEE JOINT

PRIORITY CLAIM

This is a U.S. national stage of application No. PCT/DE00/04180, filed on Nov. 24, 2000. Priority is claimed on that application and on the following applications: Country: Germany, Application No.: 199 61 915.8, Filed: Dec. 21, 1999; Country: Germany, Application No.: 100 26 440.9, Filed: May 29, 2000.

BACKGROUND OF THE INVENTION

The invention relates to a multiaxis joint, especially an artificial knee joint, whose axes of rotation are perpendicular to one plane.

DESCRIPTION OF THE RELATED ART

In prosthetics, artificial knee joints are known which swivel about a single axis, their respective swiveling movement being unsatisfactory, and which in particular permit only an unnatural gait pattern. Multiaxis knee joints have therefore been disclosed whose axes are perpendicular to one plane, for example in accordance with U.S. Pat. No. 5,314,498.

In multiaxis knee joints of this type, a polar curve describes the relative movement of the instantaneous center of rotation during swiveling. In this way, a harmonious gait pattern is obtained, because walking on uneven surfaces and stepping over small obstacles and the like is made easier by a shortening of the knee joint. To do this, the leg has to be consciously lifted and, in the process, the instantaneous center of rotation generally shifts forward before the joint comes into the actual flexion angle. In this forwardly directed movement, the points of articulation move away from one another, which results in a lengthening of the knee joint. One reason for this, among others, is that the polar curve and thus the instantaneous center of rotation generally lies outside the actual knee joint. In this respect, an unnatural pattern of movement is also produced here, because the leg which is actually to be shortened is first lengthened and must therefore be lifted higher than an obstacle or the normal pattern of movement actually requires.

SUMMARY OF THE INVENTION

Against this technical background, the invention has the object of making available a multiaxis joint, especially an artificial knee joint, which permits a harmonious gait modeled after the natural function of a knee.

To achieve this object in a multiaxis joint, especially an artificial knee joint, whose axes of rotation are perpendicular to one plane, a relative swiveling of an upper platform toward a lower platform from a rest position to a position of maximum excursion is permitted, upon which swiveling the distance between the platforms is immediately reduced with an excursion from the rest position. The polar curve which describes the relative movement of the instantaneous center of rotation will as a result also immediately describe a convergence of the two platforms which are attached to a thigh and lower leg, respectively. Thus, upon a walking movement and a lifting of the prosthesis, the distance between a ground surface and a foot of the prosthesis is immediately increased to such an extent that irregularities and small obstacles can be surmounted in an almost natural way.

In particular, it is also provided for here that, during the swiveling of the platforms relative to one another, the instantaneous center of rotation at all times lies inside the actual joint.

Here, the platforms are each understood to be an attachment element which serves to bind the joint according to the invention to a femoral stump and to a below-knee prosthesis, respectively. In this respect, the spatial configuration of the platforms is open.

In terms of construction, provision can be made for the joint to be designed to be self-retaining or self-locking in the rest position and/or the position of maximum excursion, or for these positions to be marked by dead-point positions of the joint. This affords the advantage, in particular in the rest position, that the joint is as it were locked in the respective position even when loaded. This results, on the one hand, in a stable and unstressed stance and, on the other hand, buckling of the joint upon heel contact in the walking cycle is avoided. In this respect, a particular aim is to inhibit the joint in a range of excursion from one of the positions of between 0° and 10°. Nevertheless, initiation of the flexion phase starting from the rest position, in particular also starting at 0°, is possible without any problem.

Alternatively, or in addition, provision can be made for the rest position and/or the position of maximum excursion to be fixed by one or more limit stops. Such limit stops guarantee that the swiveling can take place only within a predetermined angle range. By means of a limit stop, it is also possible for a considerably greater load to be taken up by the joint in said positions. It has proven expedient to provide for a cushioned run-in into the rest position and/or the position of maximum excursion. In this connection, it is conceivable on the one hand to provide special dampers, for example also on limit stops, or in some other way to reduce the angular velocity of the axes of rotation during the run-in into the positions. A cushioned, gentle run-in into one of the positions can also be achieved by the predetermined kinematics of the joint itself, for example by the run-in into self-retaining, self-locking areas or dead-point positions.

In terms of construction, provision is made for the platforms to be connected by two levers of different length articulated respectively at their ends on the platforms.

This measure ensures that the upper platform is displaced variably not only in height relative to the lower, but that the platforms are actually swiveled about an angle relative to one another. As a further construction measure, provision can be made that in one position, in particular in the rest position, the opening angle of the lines connecting the axes of the levers is less than 95°, and in particular these can also be approximately perpendicular to one another. In this respect, it is preferable that, in this position in particular, an axis of the second lever is arranged lying substantially on the connecting line of the axes of a first lever. A setting of the joint is thus obtained such that in normal standing, when the joint assumes the rest position, a stable and unstressed stance is guaranteed. This up to and including a certain excursion, if loading takes place in this excursion.

In this respect, it is also preferably provided that, during the swiveling, the levers cross each other, or at least in continuation the connecting lines of the first and second axes. These measures ensure, inter alia, that the instantaneous center of rotation during swiveling lies inside the joint according to the invention and that, as a consequence, an approximately natural pattern of movement is obtained.

In a further embodiment, it is provided that in one position, in particular in the rest position, the first axes of the levers articulated on the lower platform are arranged substantially at the same height or, alternatively, that a first axis of a lever articulated on the lower platform is arranged lying higher than the first axis of the other lever. Opposite the plane spanned by these two first axes in one position, in particular in the rest position, an angle of between 45° and 75°, in particular of between 50° and 60°, is preferably spanned between the first lever and this plane. This is the angle between the line connecting the axes of the first lever and the line connecting the first axes in the lower platform.

These construction measures are geared toward the natural attachment of the cruciate ligaments to the lower leg, and the natural articulation of the anterior cruciate ligament on the lower leg in the standing position. Corresponding to the distance between the attachment of anterior and posterior cruciate ligament to the lower leg, it is also preferably provided that the distance between the first axes is between 36 mm and 62 mm. Likewise, the distance of the first axis from the second axis of the first lever articulated on the upper platform can be between 45 mm and 80 mm, once again geared toward the length of an anterior cruciate ligament between thigh and lower leg of a person of average height. Corresponding to the distance between the attachment of the cruciate ligaments to the thigh, a distance between the second axes of between 16 mm and 46 mm is provided. The simulation of the human knee in respect of the cruciate ligaments is completed by the fact that, corresponding to the length of the posterior cruciate ligament, the distance of the first axis from the second axis of the second lever articulated on the upper platform is between 27 mm and 62 mm.

As a result of these construction measures, the situation is also achieved that in the rest position, i.e. in the standing position, the line of the principally vertical loading of the joint extends lying preferably between the two upper axes, and possibly also slightly in front of the second axis of the second lever, viewed in the direction of swiveling, but which line is actually crossed by the levers.

Corresponding to the natural movement, a restriction on the excursion of the joint is also provided by means of corresponding dead-point positions or limit stops at between 130° and 175°.

To ensure a sufficient stability of the knee joint according to the invention, in particular in the rest position, it is possible, as a further construction measure, to provide for one lever to be designed as a double lever. This can be the first or the second lever, or, if appropriate, both levers can be designed as double levers at the end of a common shaft for example. Such a joint then satisfies the most stringent loading requirements.

In a preferred embodiment, the joint according to the invention is provided with a counterrecoil mechanism which, when the loading of the joint is released, for example when the leg is lifted, initiates a naturally acting swivel movement. Such a counterrecoil mechanism is generally arranged between upper and lower platform, so that any forces arising only impact there.

It is expedient, in the rest position, to bind the counterrecoil mechanism vertically between the axes of the upper platform. There is sufficient space available there for construction measures, and force introduction there is also favorable for excursion of the joint as a result of the lever arrangements.

In a construction embodiment, it is provided that at least one lever of the counterrecoil mechanism is articulated on a shoulder protruding from the upper platform. As a result of this measure, the lever, even upon swiveling of the joint, is free from the upper platform. The latter may also have recesses for the at least one lever of the counterrecoil mechanism, so that the excursion needed for the joint is guaranteed. To be able to take account of individual requirements, the distance of the axis of the articulation from the upper platform is expediently adjustable.

On the lower platform, the counterrecoil mechanism is preferably bound in a central seat via the guidance of an axially spring-mounted piston, which piston has the at least one lever articulated at its free end directed toward the second platform. It is further preferred for the piston to be guided on a normal axis, which extends substantially vertically in the rest position.

For at least one axis, a brake can further be provided for slowing down a rotational movement about this axis. In the joint according to the invention, the braking of a single axis is generally sufficient since the axes are connected to one another in the manner of a joint chain.

A brake is preferred, for which independent protection is also required, in which the braking force is generated by a weight loading the joint. In the rest position in particular, the joint is then as it were locked and ensures a very stable, comfortable stance, since in this stationary rest position the loading from the body weight is at its greatest.

In a construction embodiment, it is provided that the axis is guided in a mounting which has a longitudinal slit. In the manner of known belt brakes, braking is obtained by closure of the longitudinal slit and thus frictional gripping of the axis. This embodiment of a brake, in particular for the joint according to the invention, has the advantage that it takes up very little space.

It has proven expedient to allow the weight to act on the mounting of the axis via a lever arm, in particular via a lever arm whose active lever arm length is adjustable, that is to say in particular that the site of introduction of force into the lever arm is adjustable. It may also be conceivable actually to design the physical length of the lever arm so that it is variable,
for example by turning it in a thread. It is further preferred that the weight acts counter to the force of a spring. As a result of these measures, the response of the brake and the brake operation itself can be optimally adapted to the requirements of the prosthesis wearer.

In particular, it is further provided that in one position, in particular in the rest position, a brake force can be preset so as to take account of the individual requirements of a prosthesis wearer by making it possible to preset the force needed for excursion in particular from the rest position.

The joint according to the invention is first explained in greater detail on the basis of a functional model represented in the drawing, which functional model does not reveal the actual configuration as a knee joint in the prosthesis. Thereafter, a preferred illustrative embodiment of a joint, with counterrecoil mechanism and brake, shown in the rest position, is discussed in more detail. In the drawing:

BRIEF DESCRIPTION OF THE DRAWINGS

FIG. 14 shows an isometric representation of the upper platform, FIG. 15 shows a view of the upper platform according to the arrow VI in FIG. 5, FIG. 16 shows a plan view of the upper platform according to the arrow XVI in FIG. 15, FIG. 17 shows a side view of the upper platform according to the arrow XVII in FIG. 15, FIG. 18 shows a cross section along the line IIXX, IIXX in FIG. 16, FIG. 19 shows a cross section along the line IXX, IXX in FIG. 16, FIG. 25 shows a view of a lever corresponding to FIG. 6, FIG. 26 shows a side view of the lever, FIG. 27 shows a wedge piece in a side view corresponding to FIG. 7, FIG. 28 shows a face view, FIG. 29 shows a plan view of the wedge piece according to FIG. 27, FIG. 30 shows in a view, corresponding to FIG. 7, a piston section of a counterrecoil mechanism, and FIG. 31 shows a plan view of the piston section according to the arrow XXXI in FIG. 30.

DETAILED DESCRIPTION OF THE PRESENTLY PREFERRED EMBODIMENTS

It will be expressly noted here that the following description of the functional model is reversible in its patterns of movement. In this respect, an allocation of reference labels is largely interchangeable.

Figure 1:
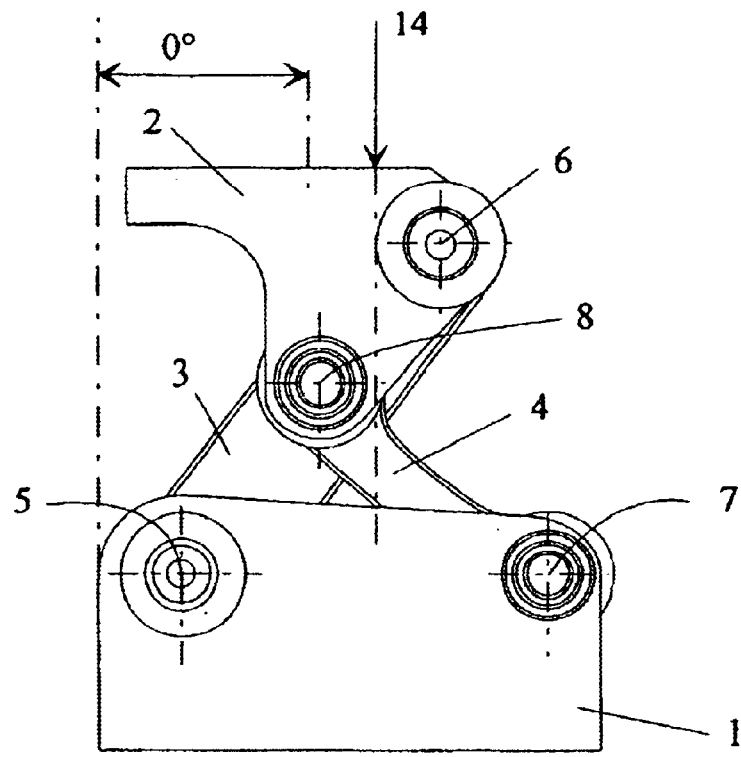
FIG. 1 shows the functional model in a rest position.
Figure 2:
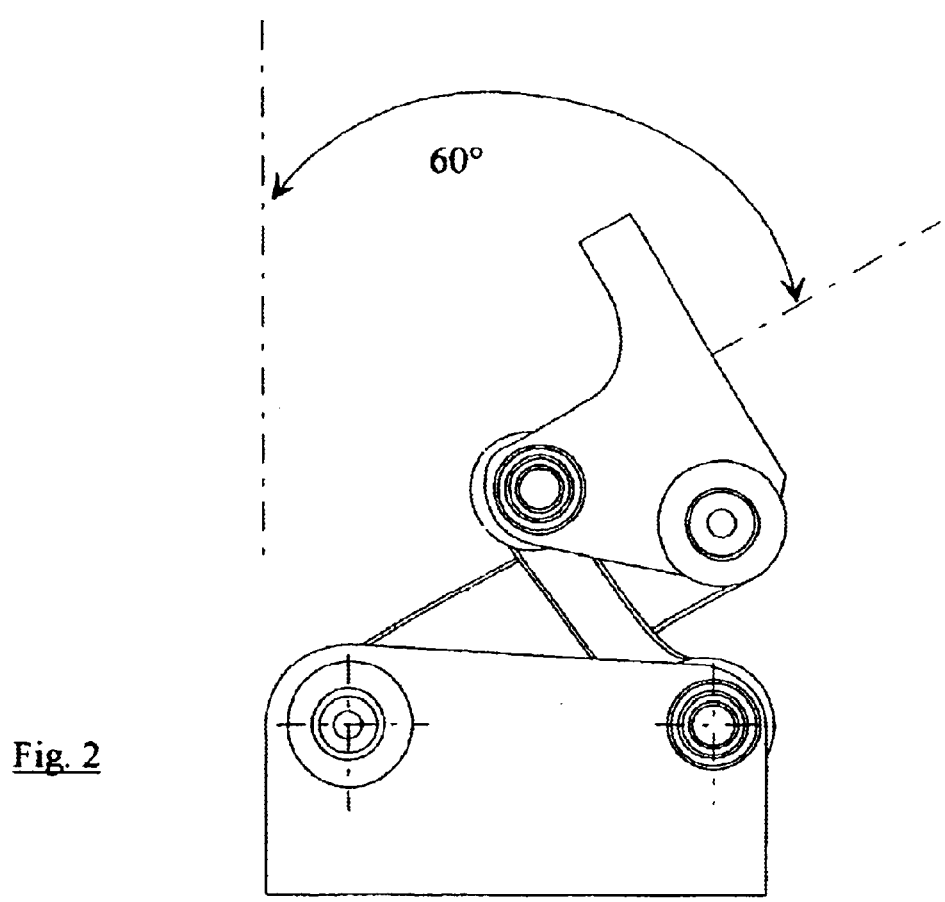
FIG. 2 shows the functional model with a 60° excursion of the upper platform relative to the lower platform.
Figure 3:
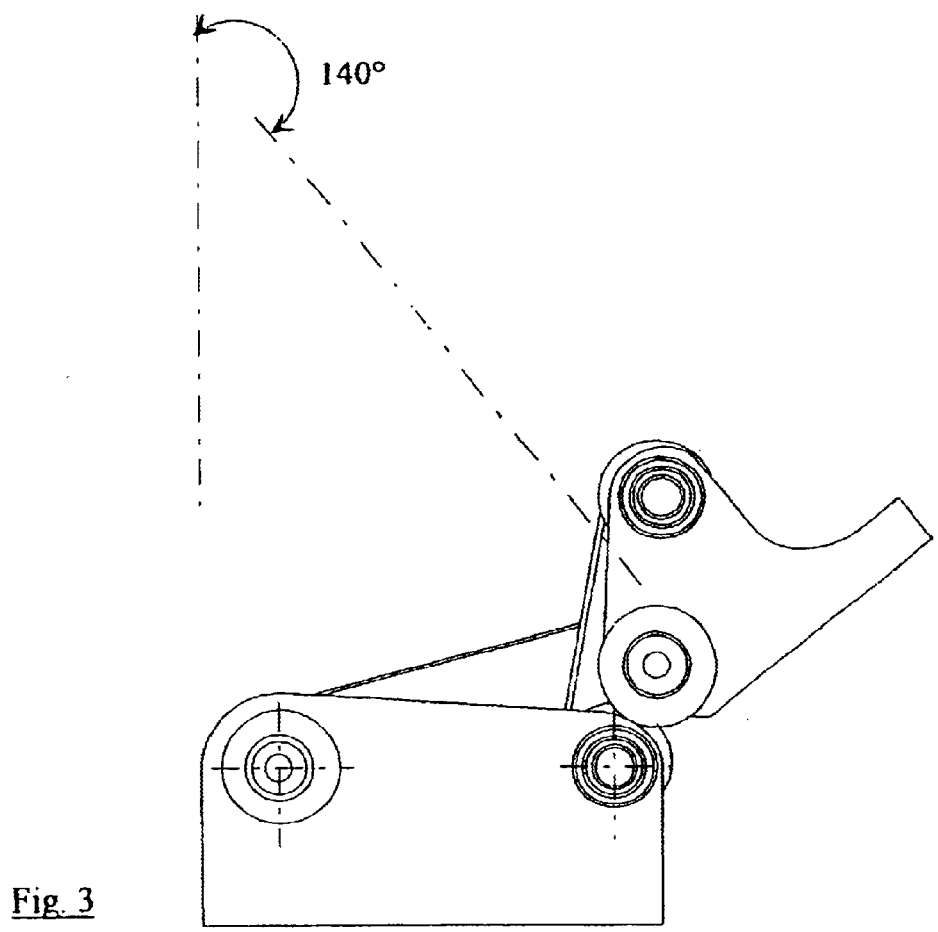
FIG. 3 shows a maximum excursion of the functional model of 140°.

FIGS. 1 through 3 show a functional model of a joint according to the invention in three different settings, where the lower platform 1 is held in a fixed position.

Accordingly, drawings 2 and 3 show an upper platform 2 adjusted relative to the platform 1.

The configurations of the platforms 1, 2 of the functional model are not explained in detail here because these can in principle be designed depending individually on the type of attachment of the prosthesis or the connection to the upper leg.

The platforms 1, 2 are connected by at least two levers 3, 4 of different length which are each articulated at their ends on the platforms 1, 2. The axes 5, 6 of the lever 3 and the axes 7, 8 of the second lever 4 are perpendicular to the plane of the drawing. This allows the joint a relative swiveling of the upper platform 2 toward the lower platform 1 from the rest position shown according to FIG. 1 to a position of maximum excursion according to FIG. 3, during which swiveling the distance between the platforms 1, 2 is immediately reduced with an excursion from the rest position according to FIG. 1. If we consider the path traveled by the axis 6, it will in fact be seen that the latter, because of the connection via the lever 3 and the axis 5 on the lower platform, moves downward on a circular trajectory 9, see also FIG. 4.

Because of the constructional design, the instantaneous center of rotation during swiveling lies inside the joint, and a very naturally acting function is thus obtained.

Figure 4:
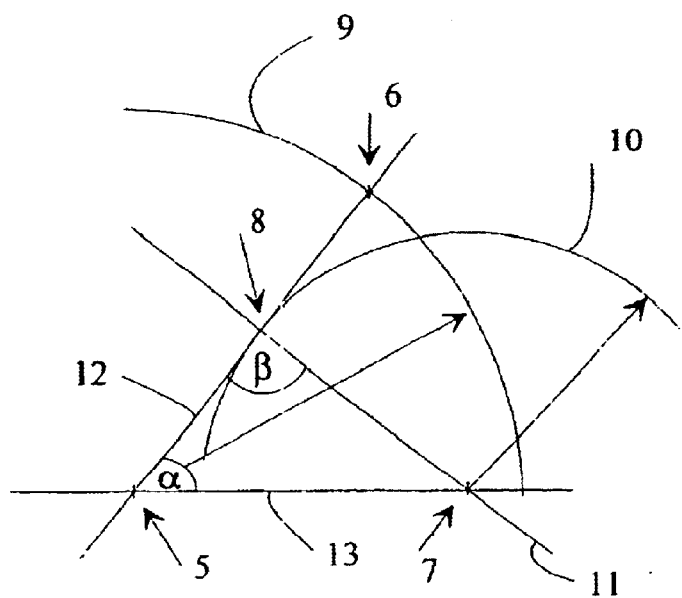
FIG. 4 shows a diagram to illustrate the patterns of movement.

The illustration according to FIG. 4 also shows that, in the rest position shown in FIG. 1, the joint should not swivel much further beyond this position. Since a further excursion of the lever 3 in FIG. 4 to the left is not possible, because the distance between the axes 6, 8 would need to increase upon further lowering of the axis 8 of the second lever 4 on the circular trajectory 10, the upper platform 2, upon further swiveling, will turn into the joint, with appropriate constructional design, in such a way that the top of the platform 2 comes to lie lowermost.

In addition to dead-point positions, self-locking and self-retaining joint positions, it is possible in particular for limit stops to fix the rest position and/or the position of maximum excursion according to FIG. 3. The run-in into these positions is expediently cushioned so that there is no hard impact on limit stops or no abrupt stop. For example, it is also conceivable to damp the angular velocity of the axes or to provide suitable shock absorbers on the limit stops.

FIGS. 1 and 4 also show that, in the rest position, the lines 11, 12 connecting the axes 5, 6 and 7, 8, respectively, of the levers 3, 4 are approximately perpendicular to one another, i.e. the angle of opening β of the lines 11, 12 is approximately 90° in the illustrative embodiment and thus less than 95°. Moreover, in the rest position, the axis 8 lies on the connecting line 12 of the axes 5, 6 of the first lever 3, said axis 8 being arranged lying approximately centrally between the axes 5, 6.

In the illustrative embodiment of the functional model, the first axes 5, 7 articulated on the lower platform 1 are arranged substantially at the same height, a horizontal line 13. In relation to this horizontal line 13, the angle of opening alpha of the line 12, and thus the setting of the lever 3 relative to the horizontal line 13, is approximately 52°, an angle alpha which lies in a range of 45° to 75°, preferably in a range of 50° to 60°, which range also describes the setting of he anterior cruciate ligament relative to a lower leg of a human knee.

However, in a variant (not shown) according to FIG. 1, a first axis of a lever can also be arranged lying deeper than the first axis of the other lever.

Correspondingly, the distance between the first axes 5, 7 of the levers 3, 4 in the lower platform 1 can preferably be between 36 mm and 62 mm. The distance of the first axis 5 from the second axis 6 of the first lever 3 articulated on the upper platform 2 also reflects the dimensions of the articulation of the cruciate ligaments and their lengths in a human knee, where this distance is between 45 mm and 80 mm.

The distance of the first axis 7 from the second axis 8 of the second lever 4 articulated on the upper platform 2 should then be between 27 mm and 62 mm, while the second axes 6, 8 in the platform 2 should be at a distance of between 16 mm and 62 mm. With such dimensions, it is possible to ensure that the maximum excursion according to FIG. 3 is approximately 140° and thus lies in a range of 130° to 150°, but which preferably reaches up to 175°, which largely corresponds to the possible swiveling movement of a human knee.

As a result of these measures, the first and second levers 3, 4, at least the respective connecting lines 12, 11 of the first and second axes 5, 6 and 7, 8, respectively, will at all times cross each other during swiveling, and the instantaneous center of rotation thus at all times lies inside the joint.

Moreover, in the rest position according to FIG. 1, the main weight load according to the arrow 14 will cross the levers 3, 4 in such a way that the line of the load lies preferably between the second axes 6, 8, or possibly slightly to the left in front of the axis 8 in FIG. 1. As a result of this, a very stable stance is also achieved since it is only with an excursion of more than about 10° that the load according to the arrow 14 no longer intersects the connecting path between the second axes 6, 8 and thus has no inhibiting action on the joint.

It should be expressly noted here that the arrangement of the levers 3, 4, for example also as double levers, is only illustrative. Thus, for example, two first levers 3 can be arranged which lie outside of the platform 1 on the end of the axis 5 and which also border the platform 2. Alternatively, or in addition, it is equally possible to design the second lever 4 as a double lever, lying inside or outside of the platforms 1, 2.

Moreover, for the function of the joint according to the invention, it is not important whether two second levers border ore or two first levers, or vice versa. If appropriate, arrangements can also be provided in which first and second levers are alternatingly arranged perpendicular to the plane of the drawing.

By means of the joint according to the invention, a joint chain is obtained in which a first lever 3 is articulated in a platform 1 via an axis 5, which first lever 3 is connected via an axis 6 to a second, upper platform 2. Lying inside the platform 2 there is a further lever arm, relatively immovable with respect to this platform, as a connection to a further axis 8 on which a second lever 4 is articulated. At the other end, the second lever 4 is in turn secured to the lower platform 1 via an axis 7. Extending inside the platform 1 there is a further lever arm which connects the first axes 5, 7 to one another. The particular kinematics of this joint are also based mainly on the dimensions of the individual lever arms.

A preferred illustrative embodiment of a joint according to the invention with brake and counterrecoil mechanism is explained in greater detail with reference to following FIGS. 5 through 31. For purposes of greater clarity, the previous position numbers will as far as possible be retained.

Figure 5:
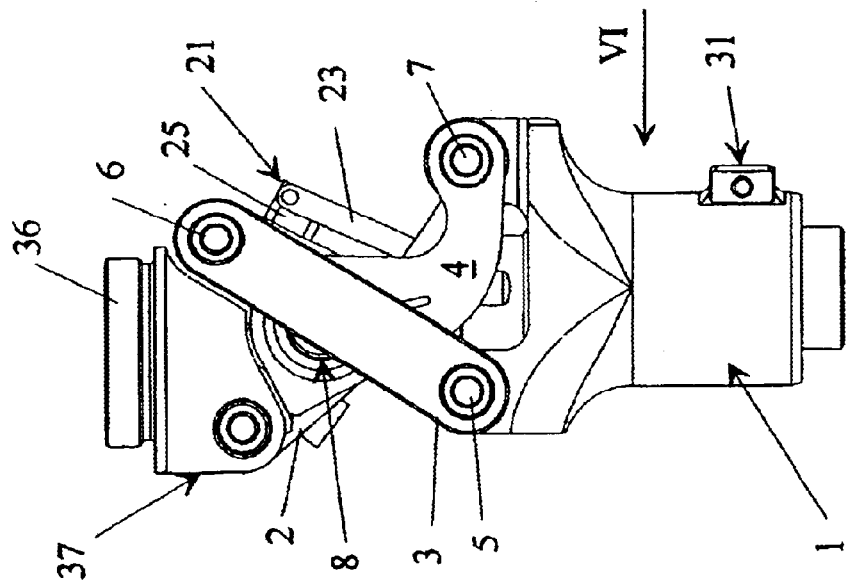
FIG. 5 shows a preferred illustrative embodiment of a joint according to the invention, in a position and view corresponding to FIG. 1.
Figure 6:
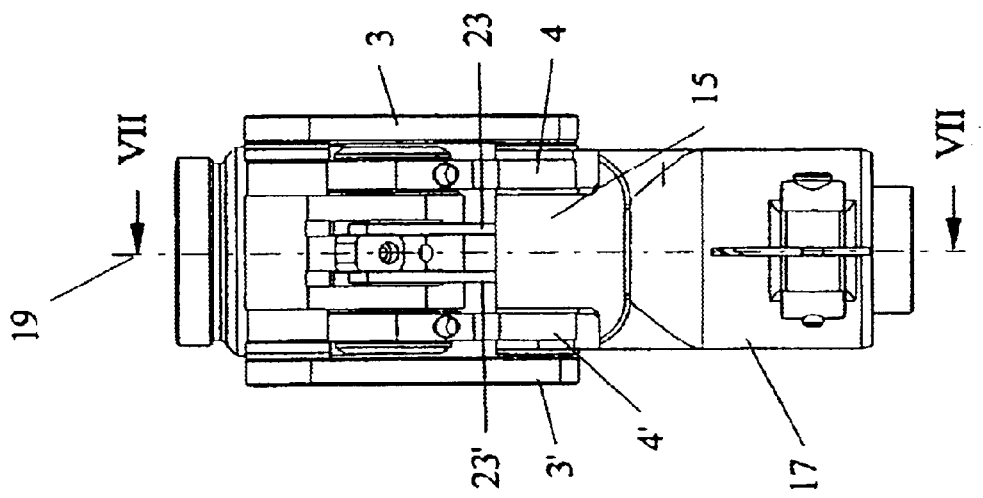
FIG. 6 shows a view of the joint according to the arrow VI in FIG. 5.
Figure 7:
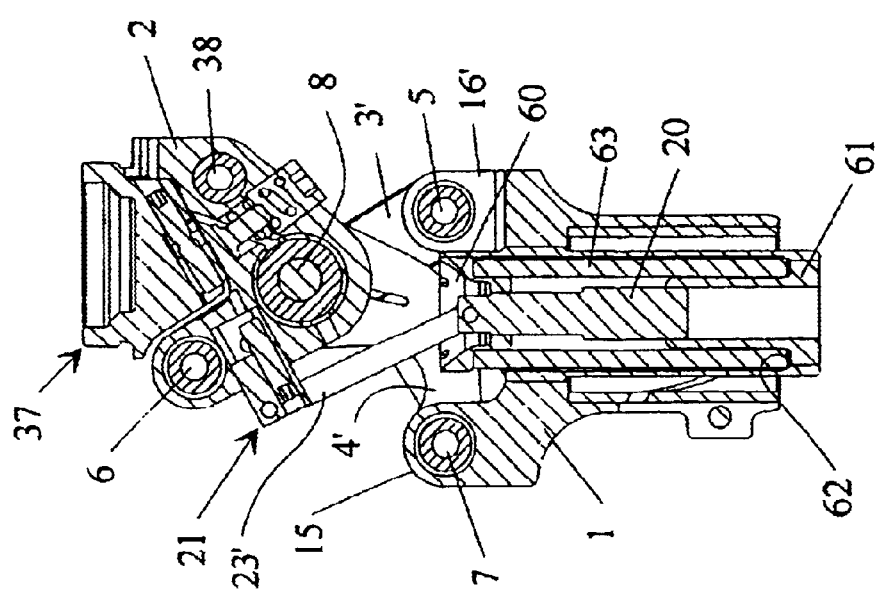
FIG. 7 shows a cross section through the joint according to the line VII, VII in FIG. 6.
Figure 8:
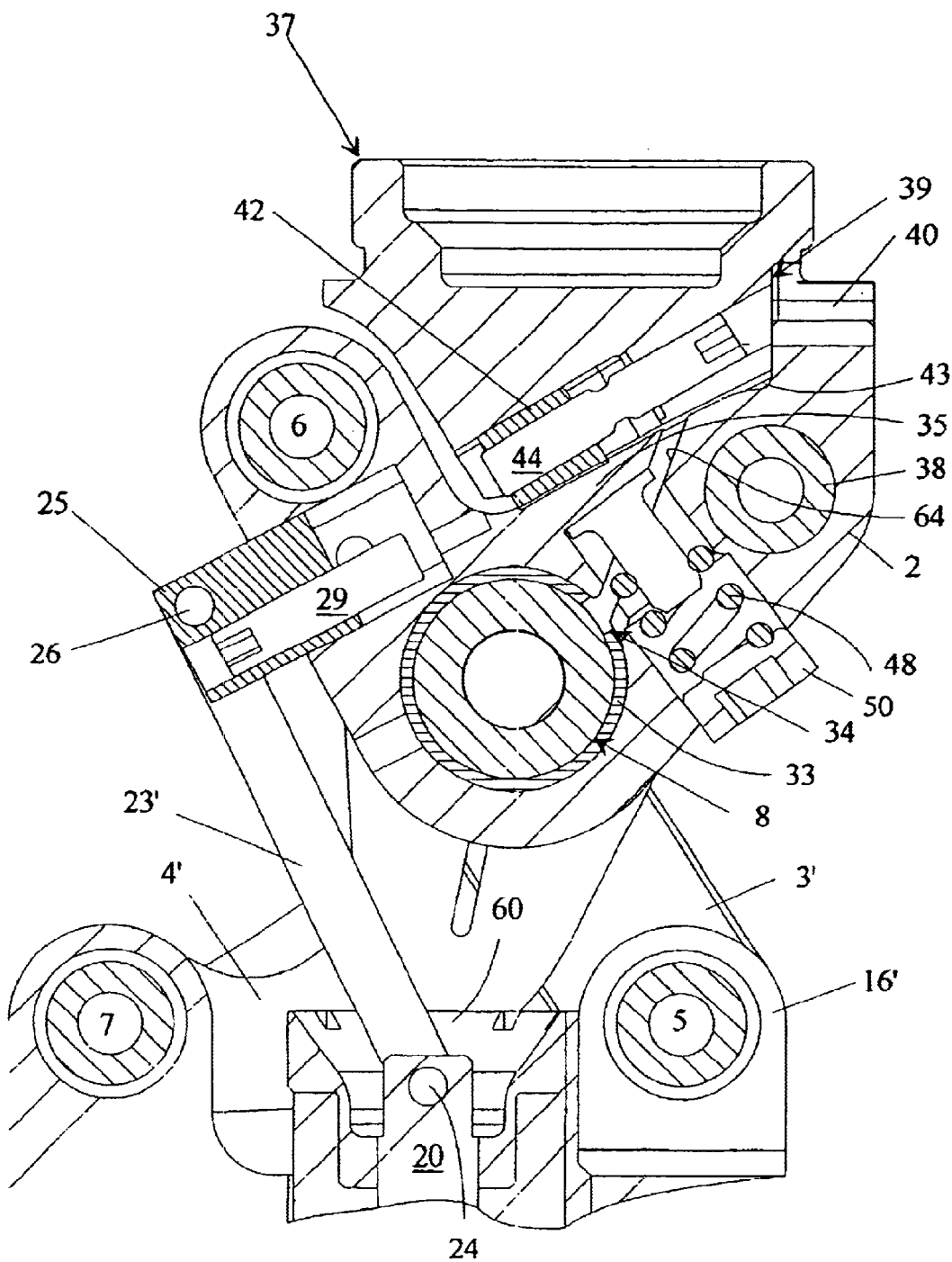
FIG. 8 shows, in an enlarged representation, a cross section according to FIG. 7 through the upper platform.
Figure 11:
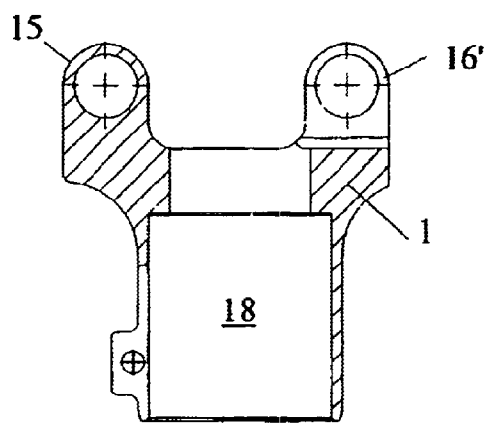
FIG. 11 shows a cross section through the lower platform according to the line XI, XI in FIG. 10.
Figure 10:
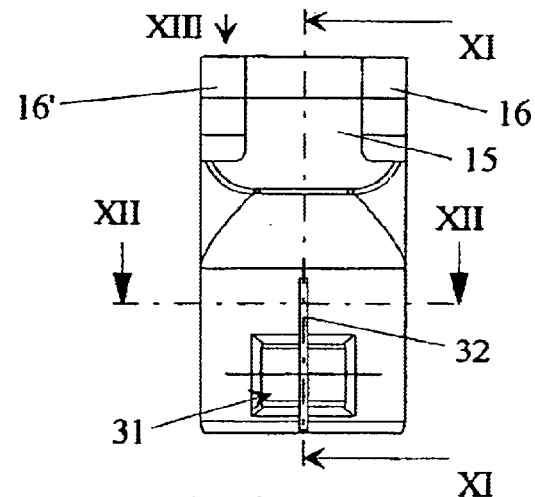
FIG. 10 shows a view of the lower platform according to the arrow VI in FIG. 5.
Figure 9:
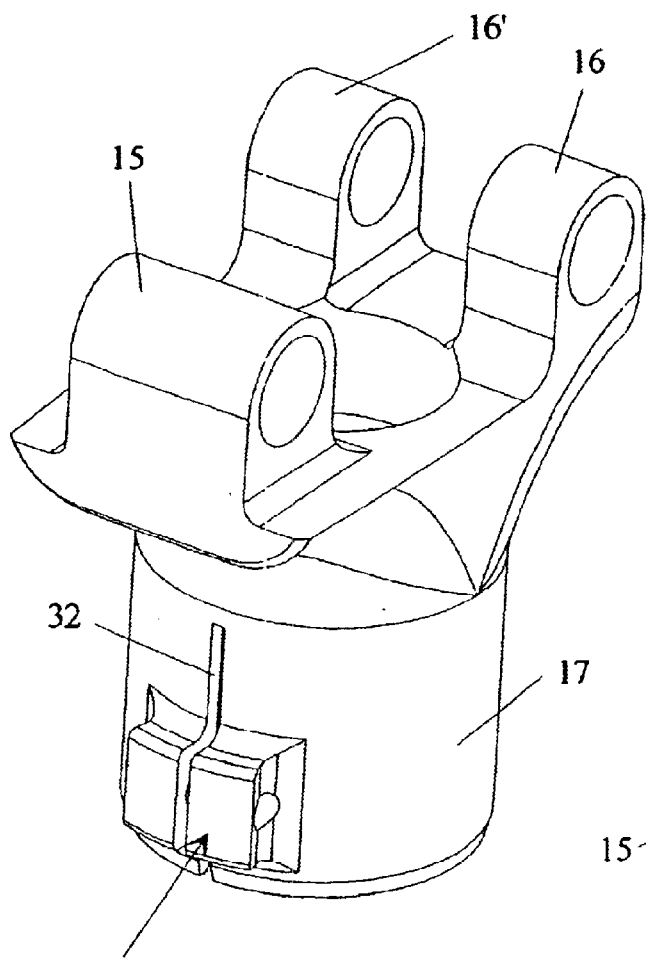
FIG. 9 shows an isometric representation of the lower platform.
Figure 12:
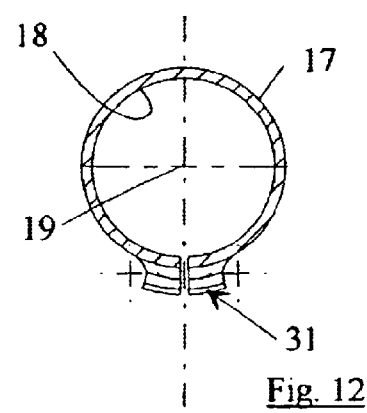
FIG. 12 shows a cross section through the lower platform according to the line XII, XII in FIG. 10.
Figure 13:
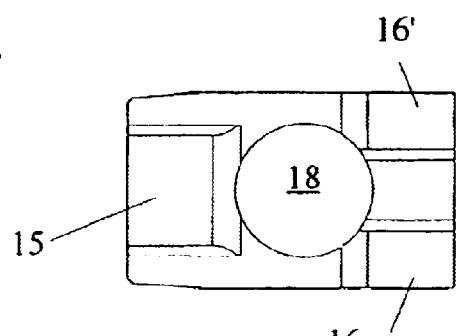
FIG. 13 shows a plan view of the lower platform according to the arrow XIII in FIG. 10.
Figure 20:
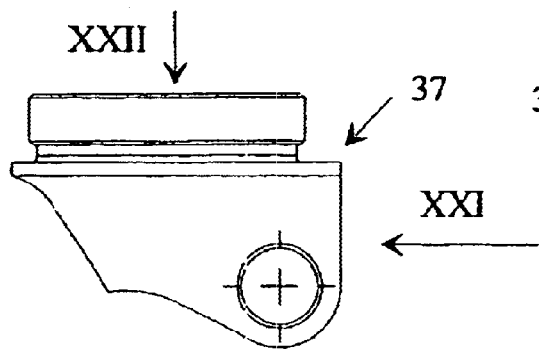
FIG. 20 shows a side view, corresponding to FIG. 7, of an attachment element for a stocking.
Figure 21:
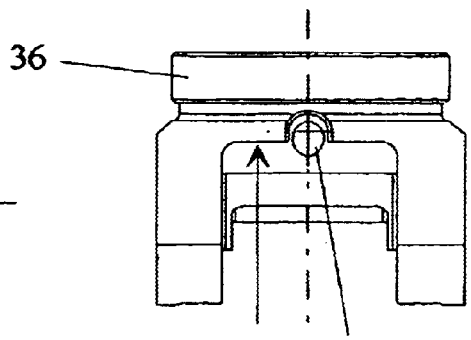
FIG. 21 shows a view according to the arrow XX in FIG. 20.
Figure 23:
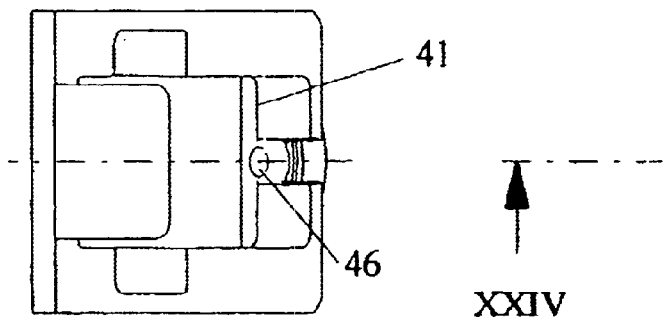
FIG. 23 shows a bottom view according to the arrow XXIIV in FIG. 24.
Figure 22:
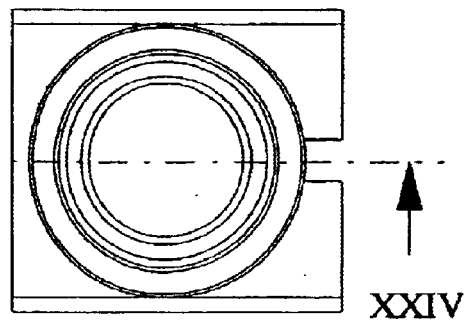
FIG. 22 shows a plan view of the attachment element according to the arrow XXII in FIG. 20.
Figure 24:
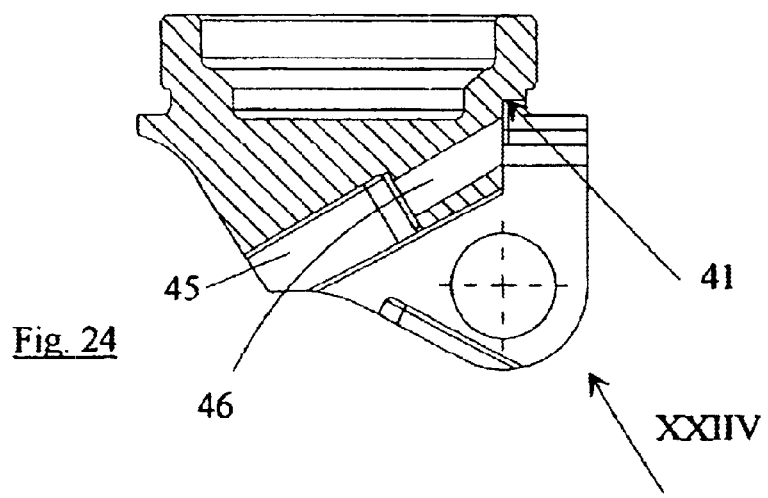
FIG. 24 shows a cross section through the attachment element along the line XXIV, XXIV in FIG. 22.

The joint shown in its rest position in FIGS. 5 through 7 is designed substantially symmetrical to its sectional plane according to FIG. 7. It has a lower platform 1 on which a double lever 3, 3' is articulated on an axis 5 and on which a double lever 4, 4' is articulated on an axis 7. The double levers 4, 4' are each designed as angle levers, see also FIGS. 25, 26. At the other end, the levers, as has been explained, are articulated on an upper platform 2 on axes 6, 8.

In the illustrative embodiment, the axes 5 through 8 are physically constituted and are securely connected to the levers 3, 3' and 4, 4'. The axes 5 through 8 are mounted so that they can rotate in mountings 15, 16, 16' of the lower platform 2, see FIG. 9. As a result, a brake of the type mentioned at the beginning can be provided for one axis, here the axis 8.

The lower platform 1, see FIGS. 9–13, has a hollow cylindrical shaft 17 through which a central seat 18 of circular cross section is defined, which is designed to be rotationally symmetrical with respect to a normal axis 19 which is substantially vertical in the rest position. A piston section 20, see also FIGS. 30, 31, is mounted in the seat 18, and, adjoining this, a castellated nut 60 of a counterrecoil mechanism 21 is axially spring-mounted and displaceable, see FIG. 7.

For this purpose, a sleeve 61 is introduced into the seat 18, and the piston section 20 is guided in the sleeve 61 at one end. At the other end, the piston section 20 passes through the castellated nut 60 which itself can be guided directly in the seat 18. Arranged between the castellated nut 60 and an annular shoulder 62 of the sleeve 61 there is a spring 63 whose pretensioning in the illustrated rest position of the joint can be adjusted by adjusting the castellated nut 60 on the piston section 20.

A double lever 23, 23' is articulated on the free end 22 of the piston section 20 lying opposite the upper platform 2, the articulation axis 24 being parallel to the other axes 5 through 8.

At the other end, the double lever 23, 23' is articulated on a shoulder 25 protruding from the upper platform 2 and can swivel about an articulation axis 26, again parallel to the axes 5 through 8. The protrusion of the articulation axis 26 from the upper platform 2 already largely ensures an unimpeded swiveling of the joint. However, depending on the excursion of the joint, it has also proven expedient for the upper platform 2 to be provided with recesses 27, 27' for the levers 23, 23', see FIG. 14.

The shoulder 25 is designed separately in an approximately cuboid shape and is received in a recess 28 in the upper platform 2. The depth of insertion of the shoulder 25 in the recess 25, and thus the distance of the articulation axis 26 from the platform 2, can be adjusted, for example by means of a screw 29, which may also serve for securing. In addition, or alternatively, the shoulder 25 can be screwed to the upper platform 2 also via bores 30, 30'.

When the load acting on the joint in the illustrated rest position is released, the force stored in the spring 62 will move the piston section 20 of the counterrecoil mechanism 21 upward. The force will be transmitted via the shoulder 25 to the upper platform 2 by means of the double lever 23, 23' articulated on the piston section 20, and the upper platform 2 will swivel relative to the lower platform 1. In the rest position, the weight will generally be sufficient to tension the spring 62 and to counteract the force of the spring 62. In the counterrecoil mechanism 21 too, a movement reversal is in principle possible through another choice of spring bearing.

The hollow cylindrical shaft 17 is also used to receive an attachment piece of a prosthesis (not shown). Joint and prosthesis are locked together, for example, by means of a tensioning lock 31 covering an axial gap 32.

In the preferred illustrative embodiment, a rotational movement of the axis 8 is also provided which is slowed by a braking device of the type mentioned at the outset.

For this purpose, the axis 8 is mounted in a mounting 33 in the upper platform 2, said mounting 33 having a slit 34 which passes through the upper platform 2. In the illustrative embodiment, the mounting 33 is therefore limited to a simple axially slit tube. By reduction of the gap distance, the axis 8 is braked frictionally in the mounting.

By continuing the slit 34 as gap 64 in the upper platform 2, a lever arm 35 is formed via which the weight acts on the mounting 33. The weight is applied via an attachment 36 known per se for example for a stocking of the prosthesis wearer.

The attachment 36 is part of a separately designed attachment element 37, see FIGS. 20 through 24. This attachment element appears to be able to swivel about a bolt 38 relative to the upper platform 2. The fact is, however, that by means of the special design of the bearing, see arrow 39 in FIG. 8, between a contact angle 40 of the upper platform 2 and a back angle 41 of the attachment element 37, a swiveling relative to one another is made impossible. Since the rest of the attachment element 37 stands free above the top side of the lever arm 35 of the upper platform 2, the attachment element 37 acts, owing to flexural stresses, in the manner of a lever arm which, via a wedge piece 42, transmits the weight arising on the attachment 36 to the lever arm 35 of the upper platform 2. The apparent axis of rotation of the attachment element 37 is here essentially marked by a foot 43 supported in a corresponding recess of the platform 2.

The position of the wedge piece 42 transmitting force further, see FIGS. 27–29, can be changed along the axis of the screw 44 provided for this purpose in a recess 45 guiding the wedge piece 42 in the attachment element 37. In order also to be able to make adjustments to a finished joint, the attachment element also has, in the axial continuation of the screw 44, a bore 46 which continues in a depression 47 of the contact angle 40 of the upper platform 2.

By displacement of the wedge piece 42, or of two wedge pieces relative to one another, a prestressing can further be applied via the lever arm 35 to the mounting 33, and a braking force can thus be preset in particular for the rest position.

By changing the position and thus also the different angle setting of the top side of the lever arm 35 and of the attachment element, or by applying different prestressing, and also the active length of the lever arm 35 which can be set as a result of this, it is possible to achieve an individual adaptation of the response and characteristics of the brake. This is assisted by a spring 48 which relieves the lever arm 35 and whose pretensioning can be adjusted and which is held in a bore 49 by an adjusting screw 50.

It may be desirable, however, for a rotational movement of the joint still to take place when a large braking force is applied. For this purpose, suitable measures, for example in the form of a slip clutch, can be provided between the axis 8 fixed by the brake and the connections to the levers 4, 4', or alternatively between the upper platform 2 and the mounting 33. With suitable force application and suitable choice of material, slipping may also occur within the mounting.

This is achieved by the measure of connecting the levers 4, 4' to the axis 8 according to FIGS. 25, 26 by means of a seat 52 which has a slit 51. Via a screw, bolt or the like introduced into a bore 53, it is then possible, by adjusting the slit width, to adjust in a characteristic manner the forces transmitted from the connection of the levers 4, 4' to the axis 8. A further bore 54 is used to receive a fastening screw for the mounting 33.

What is claimed is:

1. A multiaxis prosthetic joint comprising
a lower platform, and
an upper platform which is connected to said lower platform by first and second levers having parallel axes of rotation which permit swiveling said upper platform from a rest position to a position of maximum excursion relative to said lower platform, each said lever having a pair of ends, each said lever being articulated at one of said ends about a first axis on said lower platform and a second axis on said upper platform, wherein each said lever comprises a connecting line connecting respective said first and second axes, said connecting line of said second lever being shorter than said connecting line of said first lever, wherein said connecting lines of said first and second levers cross over each other at all times during swiveling between said rest position and said position of maximum excursion.

2. A multiaxis prosthetic joint as in claim 1 wherein said upper platform rotates about an instantaneous axis of rotation during swiveling of said platforms relative to one another, said instantaneous axis of rotation lying inside said joint.

3. A multiaxis prosthetic joint as in claim 1 wherein said joint is one of self-retaining and self-locking in at least one of said rest position and said position of maximum excursion.

4. A multiaxis prosthetic joint as in claim 1 further comprising at least one stop for fixing at least one of said rest position and said position of maximum excursion.

5. A multiaxis prosthetic joint as in claim 1 further comprising means for cushioning run-in into at least one of the rest position and the position of maximum excursion.

6. A multiaxis prosthetic joint as in claim 1 wherein said connecting lines of said first and second levers form an opening angle of less than 95 degrees when said joint is in said rest position.

7. A multiaxis prosthetic joint as in claim 1 wherein second axis of said second lever lies on said connecting line of said first lever when said joint is in the rest position.

8. A multiaxis prosthetic joint as in claim 1 wherein the first axes are arranged at the same height when said joint is in the rest position.

9. A multiaxis prosthetic joint as in claim 1 wherein the first axes are arranged at the different heights when said joint is in the rest position.

10. A multiaxis prosthetic joint as in claim 1 wherein said connecting line of said first lever forms an angle of between 50 and 60 degrees with a line connecting said first axes when said joint is in the rest position.

11. A multiaxis prosthetic joint as in claim 1 wherein said first axes are separated by a distance between 36 mm and 62 mm.

12. A multiaxis prosthetic joint as in claim 1 wherein the first and second axes of the first lever are separated by a distance between 45 mm and 80 mm.

13. A multiaxis prosthetic joint as in claim 1 wherein the first and second axes of the second lever are separated by a distance between 27 mm and 62 mm.

14. A multiaxis prosthetic joint as in claim 1 wherein said second axes are separated by a distance between 16 mm and 46 mm.

15. A multiaxis prosthetic joint as in claim 1 wherein said platforms can swivel through a maximum excursion angle of between 130 degrees and 175 degrees relative to each other.

16. A multiaxis prosthetic joint as in claim 1 wherein one of said first and second levers is a double lever.

17. A multiaxis prosthetic joint as in claim 1 further comprising a counter-recoil mechanism arranged between said lower platform and said upper platform.

18. A multiaxis prosthetic joint as in claim 17 wherein said counter-recoil mechanism is bound between said second axes when said joint is in the rest position.

19. A multiaxis prosthetic joint as in claim 17 wherein said upper platform has a shoulder protruding therefrom, said counter-recoil mechanism comprising at least one lever articulated about an axis on said shoulder.

20. A multiaxis prosthetic joint as in claim 19 wherein said shoulder is adjustably mounted on said upper platform so that the position of said axis on said shoulder relative to said upper platform can be adjusted.

21. A multiaxis prosthetic joint as in claim 19 wherein said lower platform has a central seat receiving an axially spring-mounted piston having a free end, said at least one lever of said counter-recoil mechanism being articulated at said free end.

22. A multiaxis prosthetic joint as in claim 1 further comprising at least one brake for slowing down rotational movement of said upper platform about at least one of said second axes.

23. A multiaxis prosthetic joint as in claim 22 wherein said brake comprises a weight which generates a braking force loading said joint.

24. A prosthetic joint as in claim 23 wherein one of said first and second axes is journaled in a mounting having an axial slit.

25. A prosthetic joint as in claim 24 further comprising an active lever arm, said weight acting on said mounting via said active lever arm.

26. A prosthetic joint as in claim 25 wherein said active lever arm is adjustable.

27. A prosthetic joint as in claim 23 wherein a brake force can be preset when said joint is in said rest position.

28. A prosthetic joint as in claim 23 further comprising a spring which counters the braking force generated by said weight.

* * * * *